United States Patent [19]
Yamada et al.

[11] Patent Number: 5,311,879
[45] Date of Patent: May 17, 1994

[54] MEDICAL DIAGNOSTIC APPARATUS UTILIZING LINE-OF-SIGHT DETECTION

[75] Inventors: Mitsuho Yamada; Hitoshi Hongo; Kenya Uomori; Hiroshi Yoshimatsu; Keiichi Ueno, all of Kyoto; Mitsuru Fujii, Hokkaido; Shinji Murakami, Hokkaido; Norihito Nakano, Hokkaido; Jiro Miyazawa, Hokkaido; Ryo Fukatsu, Hokkaido; Naohiko Takahata, Hokkaido, all of Japan

[73] Assignee: ATR Auditory and Visual Perception Research Laboratories, Kyoto, Japan

[21] Appl. No.: 995,651

[22] Filed: Dec. 18, 1992

[30] Foreign Application Priority Data

Jul. 9, 1992 [JP] Japan .................. 4-182227

[51] Int. Cl.$^5$ .............................. A61B 13/00
[52] U.S. Cl. ............................................ 128/745
[58] Field of Search ............... 128/745; 351/210, 211

[56] References Cited

U.S. PATENT DOCUMENTS

| 4,158,920 | 6/1979 | Walker | 128/745 |
| 4,838,681 | 6/1989 | Pavlidis | 128/745 |
| 4,848,340 | 7/1989 | Bille et al. | 128/745 |
| 5,070,883 | 12/1991 | Kasahara | 128/745 |

FOREIGN PATENT DOCUMENTS 2-156199 6/1990 Japan .

Primary Examiner—Max Hindenburg
Attorney, Agent, or Firm—Lowe, Price, LeBlanc & Becker

[57] ABSTRACT

In a medical diagnostic apparatus utilizing line-of-sight detection, targets are successively presented from different angles to the subject by a target presenting apparatus, eye movement of the subject while the subject is gazing at the target is detected by an eye movement detecting portion, the head movement of the subject is detected by a head movement detecting portion, and in response to the detection outputs, the spatial movement of the line-of-sight, rotation velocity component and translational velocity component of the head movement as well as the velocity component of the eye movement are calculated by a calculating portion, and the results are output to an output portion.

4 Claims, 8 Drawing Sheets

FIG. 12

MEDICAL DIAGNOSTIC APPARATUS UTILIZING LINE-OF-SIGHT DETECTION

BACKGROUND OF THE INVENTION

1. Field of the Invention

The present invention relates to a medical diagnostic apparatus utilizing line-of-sight detection, and more specifically, it relates to a medical diagnostic apparatus which enables diagnoses of diseases related to brain function such as dementia by detecting line-of-sight of a subject.

2. Description of the Background Art

The number of patients suffering from Alzheimer's disease is estimated to be four million in the United States and about a million in Japan. Compared with senile dementia such as cerebrovascular disease popular among Japanese, the cause of Alzheimer's disease is not known, and much effort has made to find the cause so as to enable early diagnosis and early medical treatment. However, it is difficult to discriminate Alzheimer's disease from cerebrovascular disease when there is no typical symptoms. There has been a strong demand of accurate method of discrimination, since development of disease, pharmaceutical treatment and so on are different for these diseases.

Hachinski's ischemic score has been proposed as a method of discriminating these two diseases. According to this ischemic score, a point is given dependent on whether or not the patient has an anamnesis of apoplexy, cerebral infraction or the like and if the points exceeds a prescribed number, it is determined as the cerebrovascular disease, and otherwise it is determined to be Alzheimer's disease. However, discrimination is still difficult by this method if the patient has no such anamnesis.

It has been known that neuropsychological symptom which is considered to be an impairment of "tool disfunction" such as visual cognitive disfunction appears from relatively early period of Alzheimer's disease. In view of this fact, Fujii et al. has reported the following analysis carried out by utilizing eye movement. More specifically, a problem of copying a cube on the right side while watching an original of the cube on the left side is presented. Even a patient who is in the initial stage I of Alzheimer's disease and does not show apparent constructional apraxia is reported to show characteristic symptom similar to a so called Balint syndrome; that is, the patient cannot stare at one point, or more specifically, abnormal distribution of gazing point appears, saccade deviated from both the presented cube and the depicted drawing by the patient is generated, or the point of gazing is fixed at the same point for a long period of time. In Alzheimer's disease, it is supposed from MRI (nuclear magnetic periorbital inspection) that there is caused disfunction of parietal lobe which is related to spatial vision. Accordingly, constructional disfunction derived from degradation in function of the rear association areas with the parietal lobe being the center, degradation of function of positional recognition of a target point or recognition of depth derived from disfunction of external spatial vision such as disfunction of eye movement, disfunction of coordinate transformation system between the coordinate of eye movement system and the coordinate of the center of one's body axis, or visual-motor disfunction, is supposed to be a possible cause of the aforementioned symptoms.

SUMMARY OF THE INVENTION

Therefore, an object of the present invention is to provide a medical diagnostic apparatus which facilitates diagnosis of diseases related to brain function by noting movement of one's line-of-sight implemented by the eye movement of the subject.

Briefly stated, in the present invention, eye movement of a subject is detected while a target is presented to the subject, spatial movement of the line-of-sight of the subject is calculated in accordance with the eye movement while the subject is looking at the target, whether or not the subject is suffering from a disease related to brain function is determined, and the calculated movement of the line-of-sight and information indicating the determination in connection with the disease related to brain function are output.

Therefore, according to the present invention, whether or not the disease is related to the brain function is determined referring to the spatial movement of the line-of-sight when the subject is gazing the target, so that the movement of the line-of-sight particular in diseases related to brain function such as Alzheimer's disease can be easily recognized, which is useful for medical and clinical diagnosis and rehabilitation.

In a more preferred embodiment of the present invention, head movement of the subject is detected, and referring to the head movement and the movement of the line-of-sight while the subject is gazing at the presented target, whether or not the disease is related to brain function is determined.

Further, in a preferred embodiment of the present invention, targets are presented from different angles with respect to the subject.

Further, in a more preferred embodiment of the present invention, rotation velocity component and parallel velocity component of the head movement of the subject are calculated and output in response to the detected head movement, and in addition, the eye ball velocity component is calculated and output in response to the eye movement of the subject.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIGS. 8(a)–(l) show an example of display in accordance with one embodiment of the present invention, which shows an example of a locus of movement of the line-of-sight provided by adding the head movement and the eye movement from 0° to 25° targets.

DESCRIPTION OF THE PREFERRED EMBODIMENTS

Figure 1:
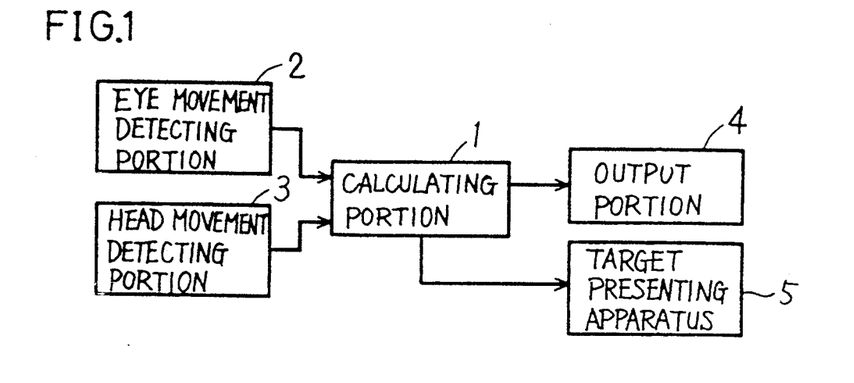
FIG. 1 is a schematic block diagram of one embodiment of the present invention.

FIG. 1 is a schematic block diagram of one embodiment of the present invention. Referring to FIG. 1, an eye movement detecting portion 2 detects eye movement of a subject, and the detection output thereof is applied to a calculating portion 1. A head movement detecting portion 3 detects the head movement of the subject, and the detection output thereof is applied to the calculating portion 1. In response to the detection output from the eye movement detecting portion 2 and the head movement detecting portion 3 when the subject is gazing at a specific target, the calculating portion 1 calculates the movement of the line-of-sight noting the movement of the line-of-sight of the subject to provide the velocity of the eye movement, the velocity of the head movement, the amplitude of the line-of-sight, characteristics of the movement of the line-of-sight, and the ratio of eye movement and of head movement in the movement of the line-of-sight, that is, head share, and the results are output to an output portion 4. A CRT display, for example, is used as the output portion 4. In addition, the calculating portion 1 provides an instruction to the target presenting apparatus 5 to have the target presented to the subject.

Figure 2:
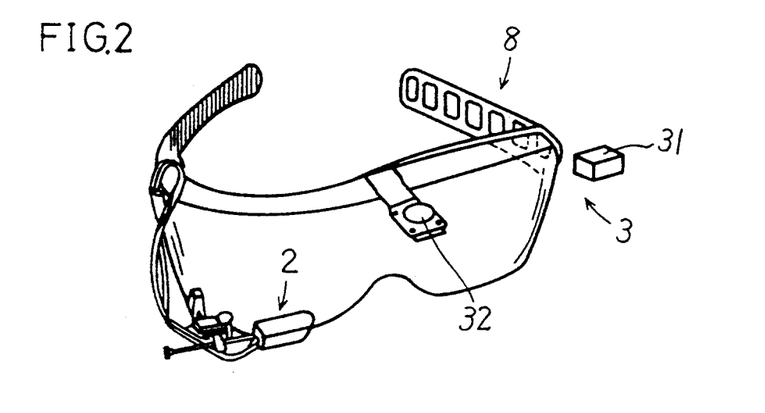
FIG. 2 shows an example in which the eye movement detecting portion and the head movement detecting portion shown in FIG. 1 are attached to goggles.
Figure 3:
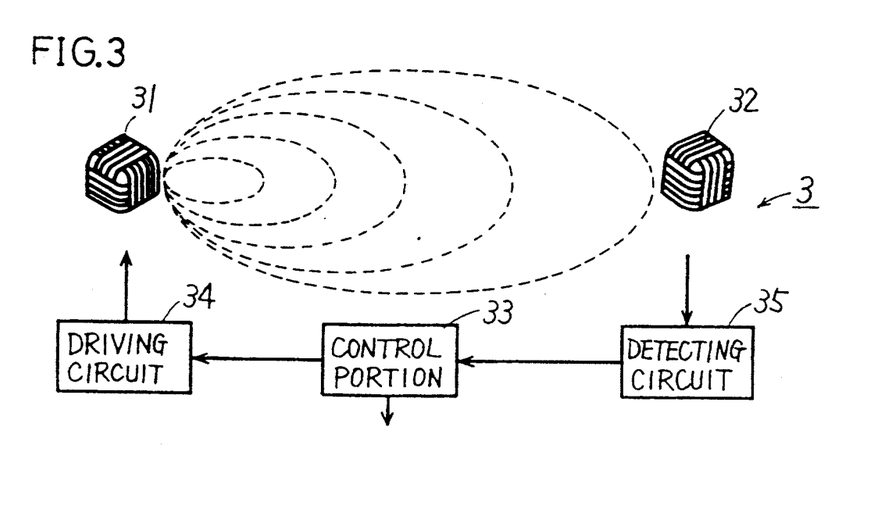
FIG. 3 shows a specific example of the head movement detecting portion.
Figure 4A:
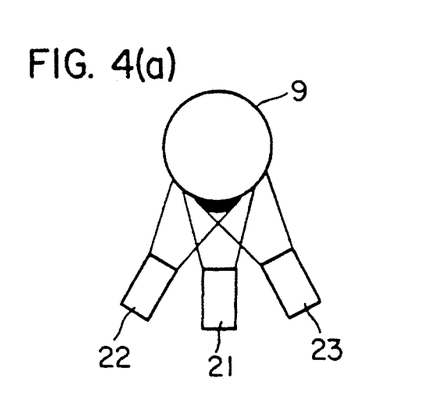
FIG. 4(a) shows a specific example of the eye movement detecting portion.

FIG. 2 shows an example in which the eye movement detecting portion 2 and the head movement detecting portion 3 shown in FIG. 1 are attached to goggles, FIG. 3 shows a specific example of the head movement detecting portion, and FIG. 4 shows a specific example of the eye movement detecting portion 2.

Figure 4B:
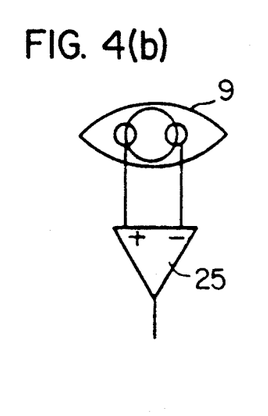
FIGS. 4(b) and 4(c) illustrate different positionings with respect to an observer's eye ball for a difference calculation and a sum calculation.
Figure 4C:
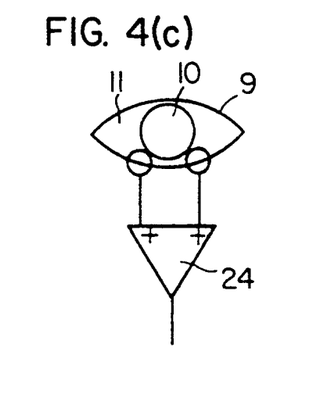

The goggles 8 shown in FIG. 2 which the subject wares have the eye movement detection portion 2 attached to a lower portion of one side thereof. The eye movement detecting portion 2 includes a light emitting diode 21 provided at the center and the photodiodes 22 and 23 provided on both sides thereof as shown in FIG. 4. A light emitting diode radiating infrared rays having relatively wide directivity of about ±21° is used as the light emitting diode 21, while ones having acute directivity of about ±10° are used as the photodiodes 22 and 23. The light beam emitted from the light emitting diode 21 to the eye ball 9 is reflected from the iris of the eye 10 and from the white of the eye 11 with different reflectivity, and the difference in reflectivity is amplified by an operational amplifier 25. If the difference is calculated, a horizontal output (left and right) is obtained as shown in FIG. 4(b), and if the sum is calculated by an operational amplifier 24, a vertical (up and down) output is obtained as shown in FIG. 4(c).

The head movement detecting portion 3 is formed of a magnetic sensor as shown in FIG. 3. More specifically, the head movement detecting portion 3 includes a orthogonal coil serving as a source 31 and an orthogonal coil serving as a sensor 32. In accordance with an instruction from a control portion 33, a driving circuit 34 drives the orthogonal coil of the source 31 to generate a magnetic field. When the subject wearing the head movement detecting portion 3 moves, a voltage is induced in the sensor 32, which voltage is detected by the detecting circuit 35, the detected output therefrom is calculated by the control portion 33, and thus data corresponding to the movement of the head is output.

Figure 5:
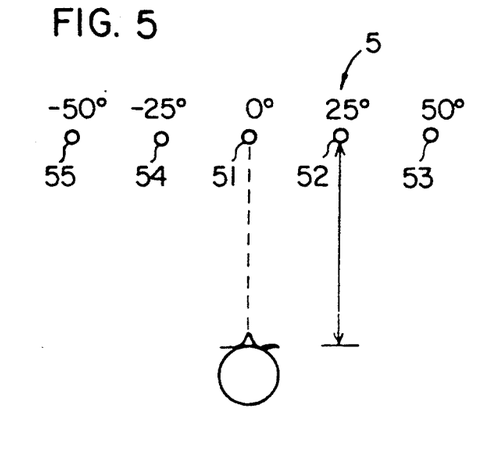
FIG. 5 is an illustration of a target presenting apparatus shown in FIG. 1.

FIG. 5 is an illustration of the target presenting apparatus 5 shown in FIG. 1. Referring to FIG. 5, a target board is provided at a position apart by 1 m from the subject, on which board light emitting diodes 51-55 are attached shifted by 25° from each other with respect to the subject at the center. The light emitting diodes 51-55 are lit in the order of 0°→25°→0°→50°=0°→−25°→0°→50°→0° in response to the instructions from the calculating portion 1 shown in FIG. 1.

Figure 6A:
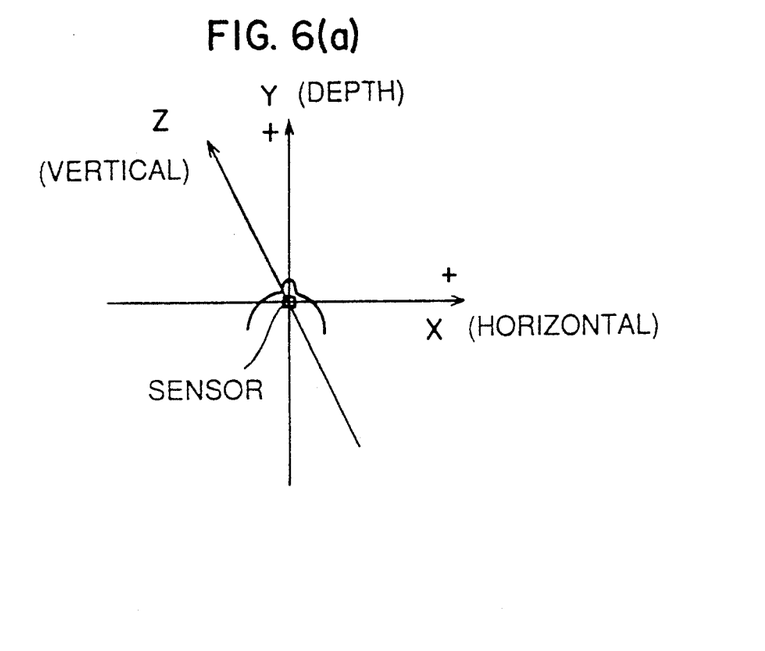
FIGS. 6(a) and 6(b) illustrate two head coordinate system with the subject being the center.
Figure 6B:
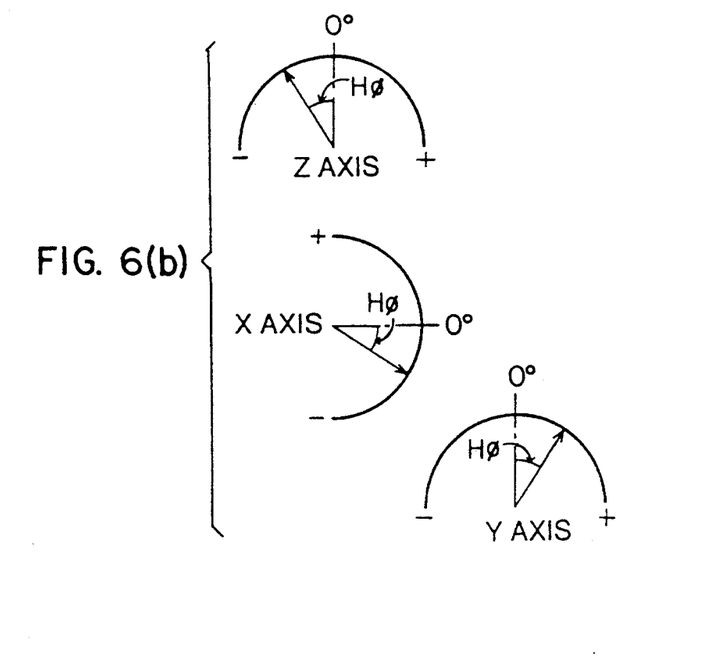

FIG. 6 is an illustration showing the principle of the head coordinate system with the subject being the center. Referring to FIG. 6, the head coordinate system detected by the head movement detecting portion 3 will be described. The head coordinate system includes two systems, that is, XY coordinate system realized by the translational movement of the subject with respect to the object of monitoring such as shown in FIG. 6(a), and a polar coordinate system based on the rotation movement of the head such as shown in FIG. 6(b). The amount of head movement in respective coordinate systems are defined as (Hx, Hy, Hz), (H$\psi$, H$\phi$, H$\theta$). In this embodiment, the direction toward the object of monitoring is represented by the Y axis, the horizontal movement is represented by the X axis and the vertical movement is represented by the Z axis, as an example. H$\phi$ represents the rotation of the X axis, that is, the movement of one's neck upward or downward. H$\theta$ represents the rotation of the Y axis, that is, the movement of inclining ones neck once from the left shoulder to the right shoulder. H$\psi$ represents rotation in the Z axis, that is, rotation of one's neck in the left or right direction.

The line-of-sight changes by the horizontal movement of the head (Hx, Hy, Hz), and when this movement is changed in the equivalent of rotation angle of the eye ball (Ex, Ey), the following equations are obtained.

$$Ex = 180/\pi \cdot \tan^{-1} Hx/(D+Hy) \tag{1}$$

$$Ey = 180/\pi \cdot \tan^{-1} Hz/(D+Hy) \tag{2}$$

where D: distance from the subject to the point of gazing.

When the neck is inclined by H$\theta$ to the left shoulder or to the right shoulder, the coordinate of the eye movement system rotates. Therefore, the eye movement coordinate system (Xe, Ye) inclined by HO must be changed to the coordinate system (Xe', Ye') which is orthogonal to the original object of monitoring.

$$Xe' = Xe \cdot \cos H\theta + Ye \cdot \sin H\theta \tag{3}$$

$$Ye' = -Xe \cdot \sin H\theta + Ye \cdot \cos H\theta \tag{4}$$

The movement of the line-of-sight (Xh, Yh) realized by the head movement is represented by the following equations (5) and (6) derived from the equations (1) and (2).

$$Xh = Ex + H\psi \quad (5)$$

$$Yh = Ey + H\phi \quad (6)$$

Therefore, the movement of the line-of-sight (Vx, Vy) taking the head movement into account is represented by the following equations (7) and (8), from equations (3) to (6).

$$Vx = Xe' + Xh \quad (7)$$

$$Vy = Ye' + Yh \quad (8)$$

By employing the equations (7) and (8) above, the ordinary movement of one's line-of-sight effected by combining head movement and eye movement can be reproduced.

Figure 7:
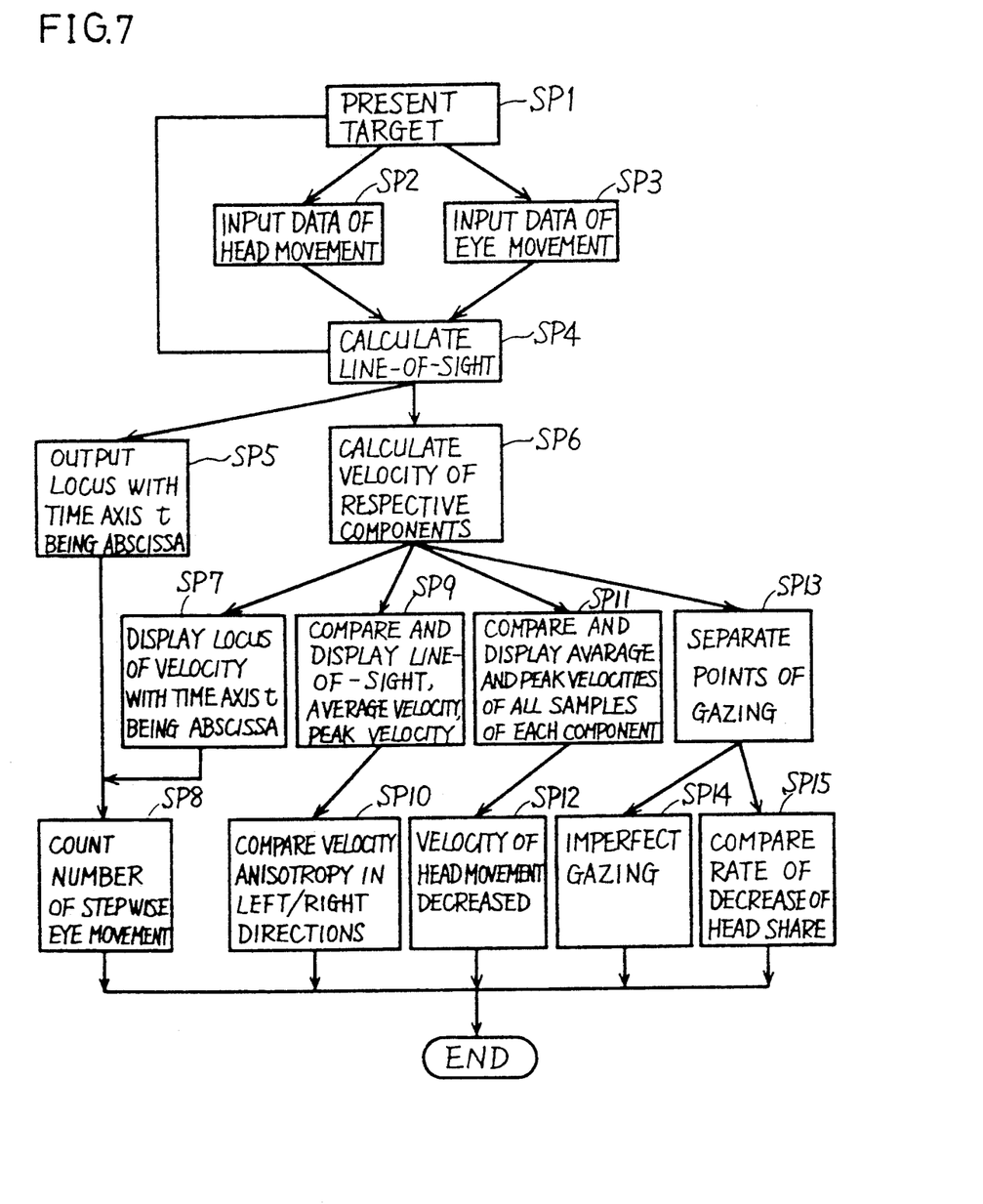
FIG. 7 is a flow chart showing specific operation of one embodiment of the present invention.

FIG. 7 is a flow chart showing the operation of one embodiment of the present invention, and FIGS. 8–12 show examples of display in accordance with one embodiment of the present invention.

Referring to FIGS. 1–12, a specific operation of one embodiment of the present invention will be described. In step (simply denoted by SP in the drawings) SP1, the calculating portion 1 in FIG. 1 have the target presenting apparatus 5 as in the same figure which presents the target to the subject. More specifically, the calculating portion 1 has the light emitting diodes 51–55 lit in the order of, for example, 0°→25°→0°→50°→0°→25°→0°→50°→0° as shown in FIG. 5, successively. At this time, the eye movement detecting portion 2 detects the eye movement of the subject, applies the data of the eye movement to the calculating portion 1. The head movement detecting portion 3 detects the head movement, and applies data of the head movement to the calculating portion 1. In step SP2, the calculating portion 1 takes the amount of head movement (Hx, Hy, Hz) and (H$\psi$, H$\phi$, H$\theta$) of the head coordinate system described above with reference to FIG. 6 as the data of head movement, and in step SP3, it takes the eye coordinate system (Xe, Ye) as the data of the eye movement. In step SP4, the calculating portion 1 effects calculation of the equations (1) to (8) described above in each of the sampling periods i, i+1, i+2 . . . . Thus, H$\psi_i$, H$\phi_i$, H$\theta_i$, Hx$_i$, Hy$_i$, Hz$_i$, X'e$_i$, Y'e$_i$, Vx$_i$ and Vy$_i$ in each sampling period are obtained.

In step SP5, the calculating portion 1 calculates the locus of the line-of-sight, the locus of the eye movement, the locus of the angle of head rotation and the locus of translational movement of the head. More specifically, the calculating portion 1 connects the line-of-sight (Vx$_i$, Vy$_i$) and (Vx$_{i+1}$, Vy$_{i+1}$) in the sampling period i, and calculates the locus of the line-of-sight. Further, the calculating portion 1 connects by the locus the eye movements (X'e$_i$, Y'e$_i$) and (X'e$_{i+1}$, Y'e$_{i+1}$) in the sampling period i, so as to calculate the locus of the eye movement. Further, the calculating portion 1 calculates the locus of the angles of the head rotation (H$\psi_i$, H$\phi_i$), (H$\psi_{i+1}$, H$\phi_{i+1}$) in the sampling period i, so as to calculate the locus of the angle of the head rotation. The calculating portion 1 connects by a locus the translational movements of the head (Ex$_i$, Ey$_i$) and (Ex$_{i+1}$, Ey$_{i+1}$) to provide a locus of the translational movement of the head.

The calculating portion 1 calculates velocities of various components in step SP6. The velocity v$_1$ of the line-of-sight is calculated by the following equation (9) where Ts represents the sampling period.

$$v_1 = \sqrt{\{(Vx_{i+1} - Vx_i)^2 + (Vy_{i+1} - Vy_i)^2\}}/Ts \quad (9)$$

The velocity v$_2$ of the eye movement is calculated by the following equation (10):

$$v_2 = \sqrt{\{(X'e_{i+1} - X'e_i)^2 + (Y'e_{i+1} - Y'e_i)^2\}}/Ts \quad (10)$$

The velocity v$_3$ of the angle of head rotation is calculated by the following equation (11):

$$v_3 = \sqrt{\{(H\phi_{i+1} - H\psi_i)^2 + (H\phi_{i+1} - H\psi_i)^2\}}/Ts \quad (11)$$

The velocity v$_4$ of the translational movement of the head is calculated by the following equation (12):

$$v_4 = \sqrt{\{(Ex_{i+1} - Ex_i)^2 + (Ey_{i+1} - Ey_i)^2\}}/Ts \quad (12)$$

Figure 8A:
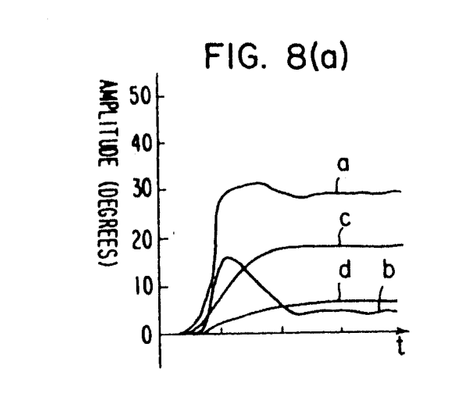
Figure 8B:
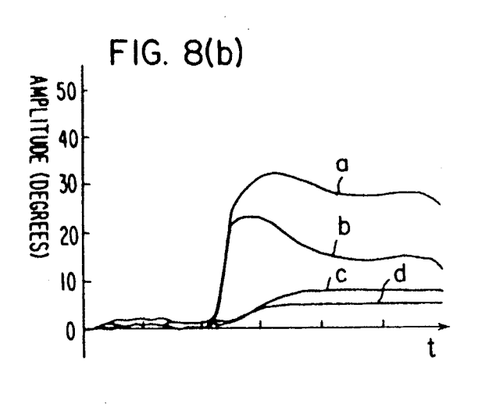
Figure 8C:
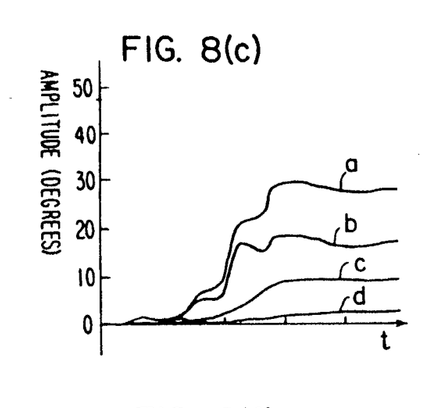
Figure 8D:
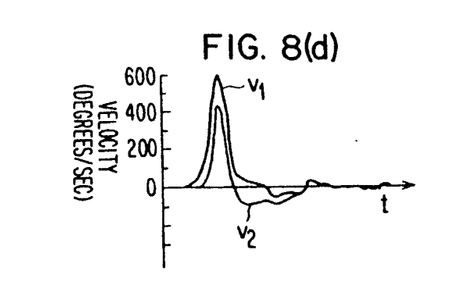
Figure 8E:
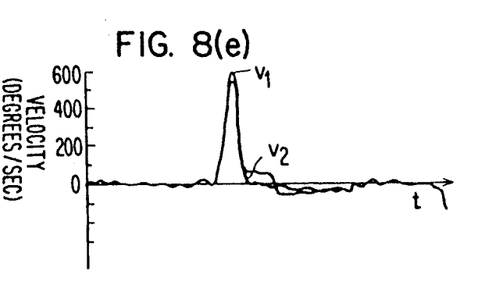
Figure 8F:
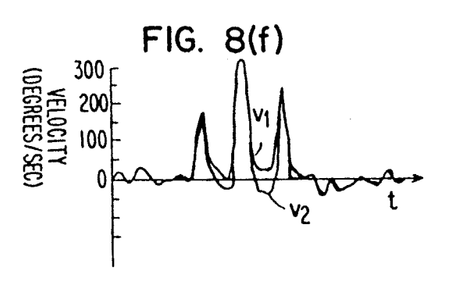
Figure 8G:
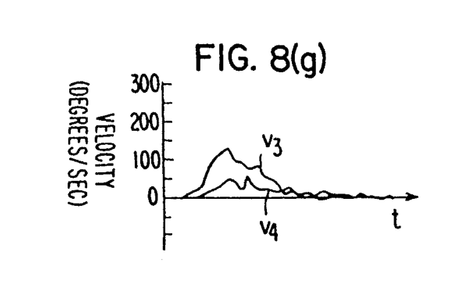
Figure 8H:
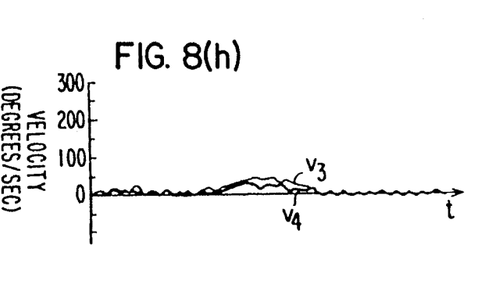
Figure 8I:
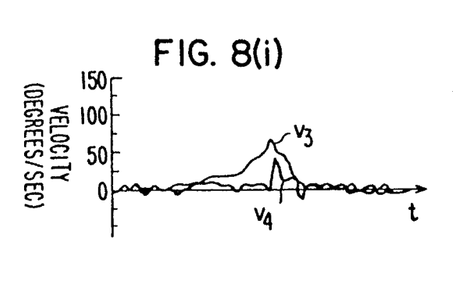

The locus a of the line-of-sight, the locus b of the eye movement, the locus c of the angle of head rotation and the locus d of the translational movement of the head calculated in the above described manner are displayed as shown in FIGS. 8(a)–(c) in step SP5, and the respective velocities v$_1$–v$_4$ are displayed as shown in FIGS. 8(d)–(i) in step SP7.

Referring to FIG. 8, (a), (d) and (g) show the data of a young healthy person. FIGS. 8(b), (e) and (h) show the data of an aged healthy person. FIGS. 8(c), (f) and (i) show data of a patient suffering from Alzheimer's disease. FIGS. 8(a)–(c) show the locus a of the line-of-sight, the locus b of the eye movement, the locus c of the angle of head rotation and the locus d of the translational movement of the head with the time axis being the abscissa. FIGS. 8(d), (e) and (f) show the velocity v$_1$ of the line-of-sight and the velocity V$_2$ of the eye movement with the time axis being the abscissa. FIGS. 8(g), (h) and (i) show the velocity v$_3$ of the angle of head rotation and the velocity v$_4$ of the translational movement of the head with the time axis being the abscissa. As is apparent from FIG. 8(c), the waveform (c+d) indicating the head movement of the patient of Alzheimer's disease is smaller than the one of the young healthy person, and as shown in FIG. 8(f), the peak of the velocity v$_1$ of the line-of-sight and the peak of the velocity v$_2$ of the eye movement of the patient of Alzheimer's disease are larger than the young and aged healthy persons. Namely, it is recognized at one sight that the patient cannot reach straight the target but he reaches the target through some steps. Dependent on whether the stepwise eye movement seen from FIGS. 8(a)–(c) or the number of peaks of the velocity of the eye movement as can be seen from FIGS. 8(d)–(f) is two or more with the average of the young healthy person being 1, the calculating portion 1 determines whether the disease comes from advance in age or the disease is Alzheimer's disease, and outputs the result to the output portion 4 in step SP8.

Figure 9A:
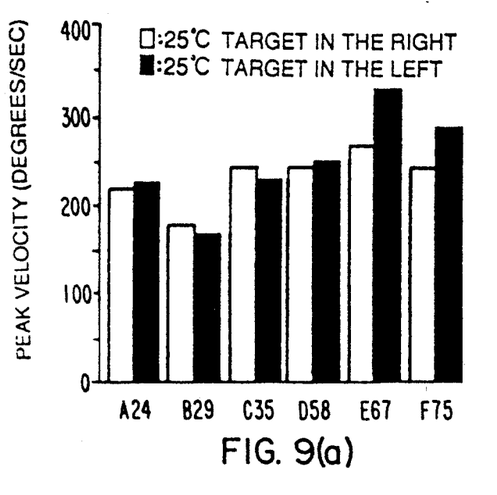
FIGS. 9(a)-(b) show an example of display of the peak velocity of the eye movement.
Figure 9B:
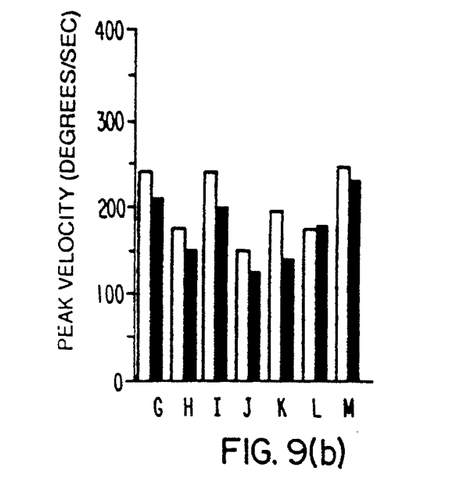
Figure 10A:
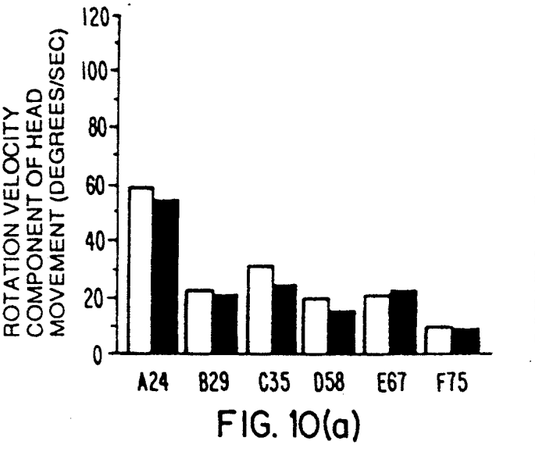
FIGS. 10(a)-(d) show rotation velocity component and the average velocity component of the head movement.
Figure 10B:
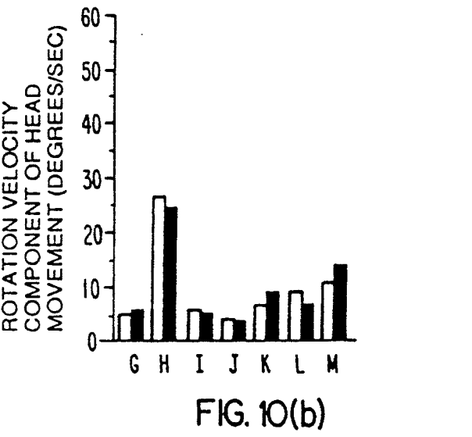
Figure 10C:
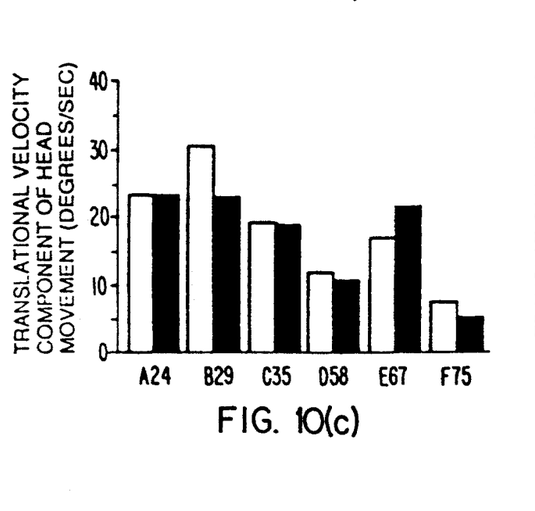
Figure 10D:
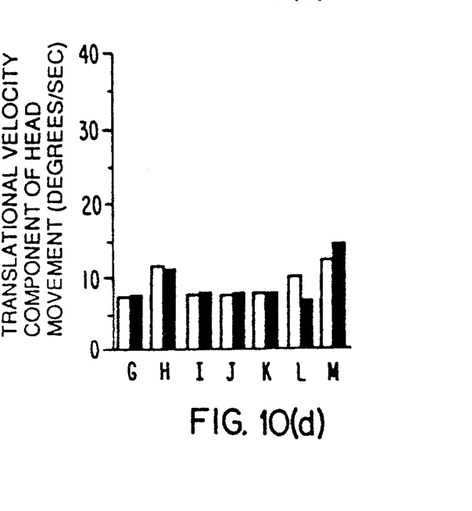

In step SP9, the calculating portion 1 calculates the peak velocity and the average velocity of the movement of the line-of-sight provided by adding samples of the head movement and the eye movement adjacent to each other on time basis, and displays the result at the output portion 4. As a result, the peak velocity is displayed in the manner as shown in FIG. 9 at the output portion 4. Further, in step SP10, the calculating portion 1 compares speed anisotropy of the left and right directions. FIG. 9(a) is an example of display of the peak velocities of six young and aged healthy persons, that is, A (24 years old), B (29 years old), C (35 years old), D (58 years old), E (67 years old) and F (75 years old) FIG. 9(b) is an example of display of the peak velocities of seven patients suffering from Alzheimer's disease. As is apparent from the comparison between FIGS. 9(a) and (b), the velocities in the left and right directions of the young and healthy persons are approximately uniform, while the velocity in the right direction is faster by 50°/sec to 100°/sec than the velocity in the left direction in the group of the patients of the Alzheimer's disease. This is used as a reference to discriminate Alzheimer's disease, and the result of discrimination is output to the output portion 4.

In step SP11, the calculating portion 1 calculates the average velocity component of the head movement, and outputs the result to the output portion 4 in the manner shown in FIG. 10. Referring to FIG. 10, (a) and (c) are examples of the healthy person, and (b) and (d) are examples of a patient suffering from Alzheimer's disease. As is apparent from FIG. 10, compared with young and old healthy persons, the patient of Alzheimer's disease have slower average velocity especially in the rotation component of the head movement. Thus, the calculating portion 1 determines whether or not the velocity of the head movement is decreased in step SP12, and discriminates Alzheimer's disease from troubles popular among old persons.

Figure 11:
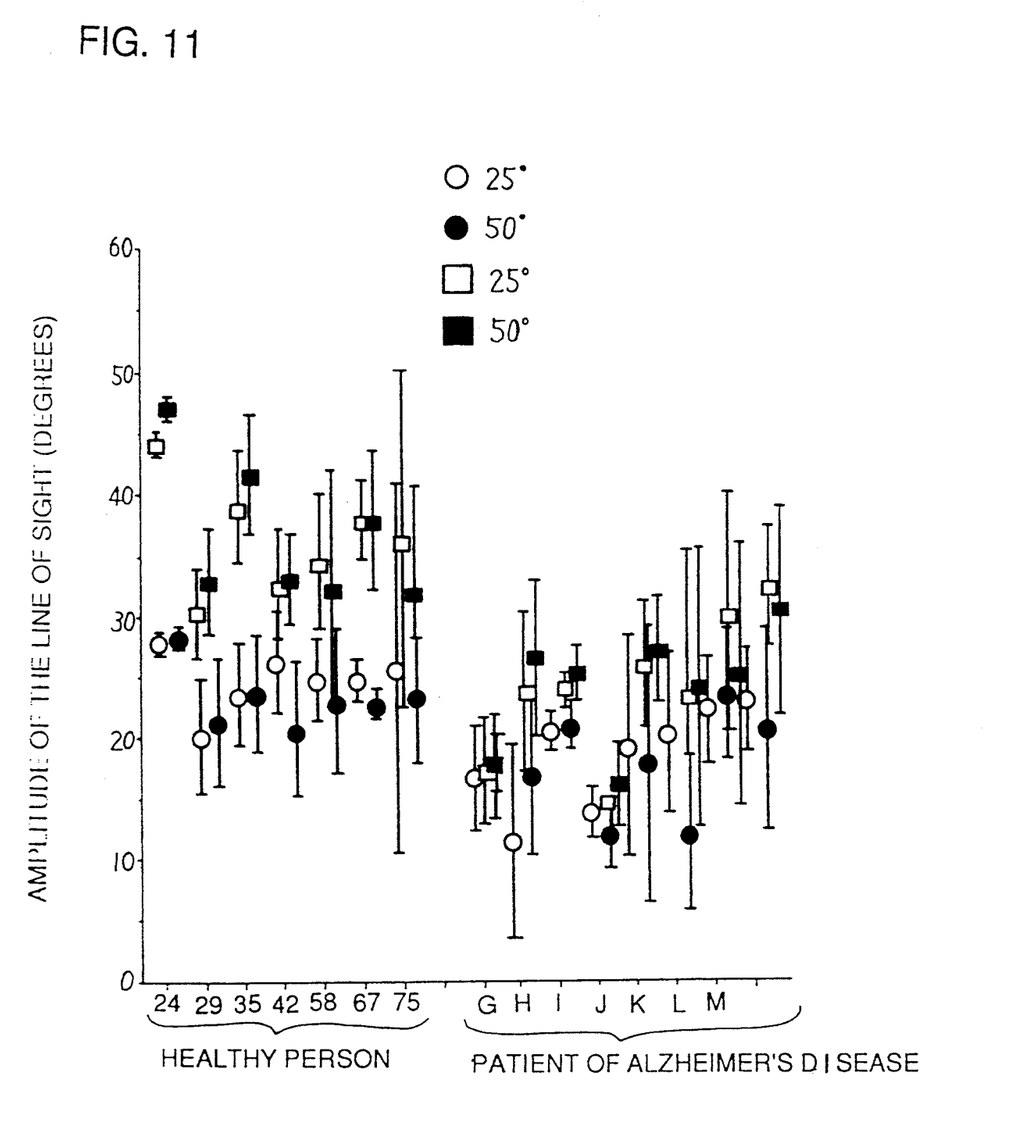
FIG. 11 shows an example of an amplitude of the line-of-sight provided by adding the head movement and the eye movement between gazing points.
Figure 12:
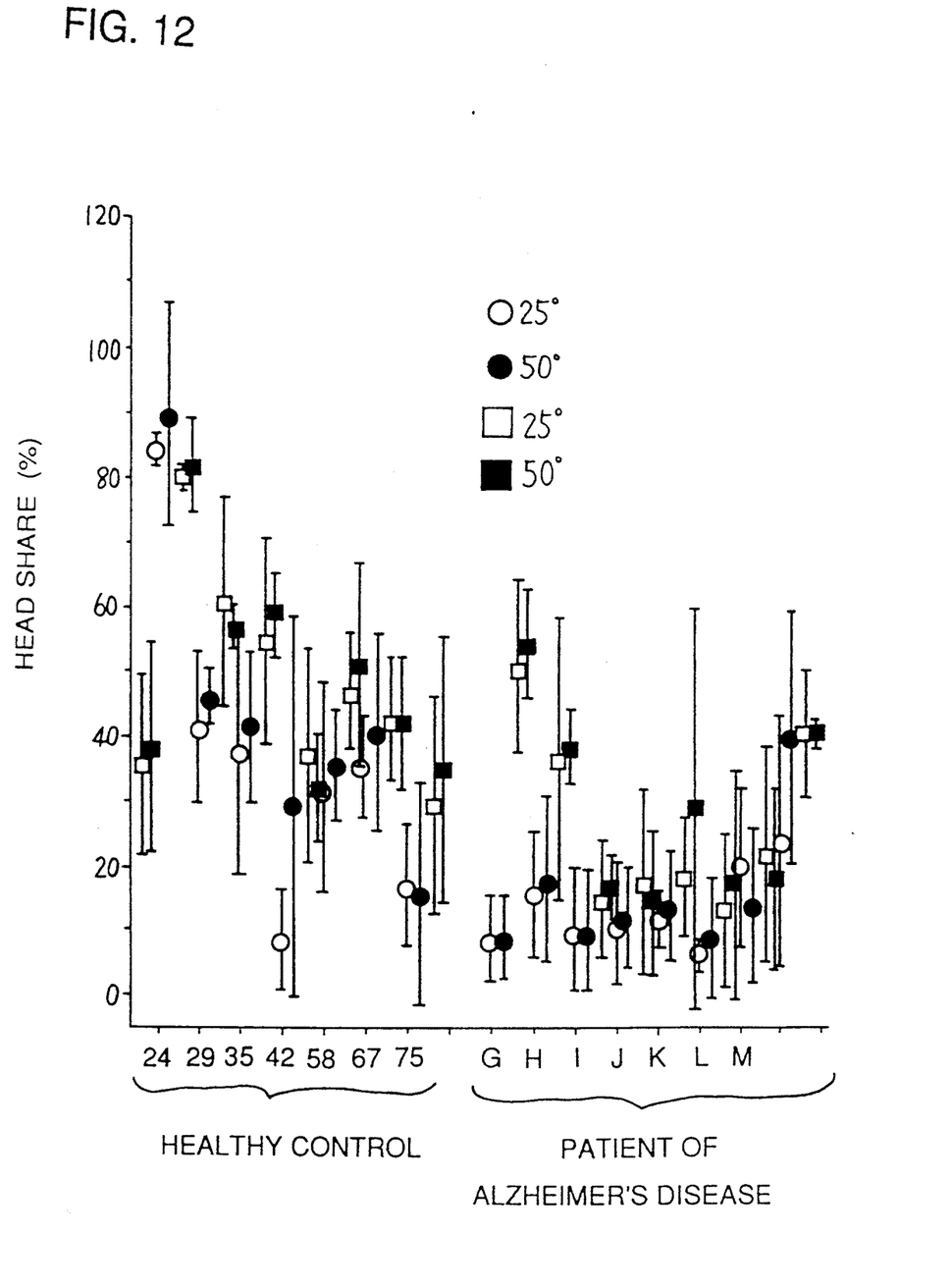
FIG. 12 shows an example of head share of the head movement with respect to the line-of-sight sight provided by adding the head movement and the eye movement between gazing points.

In step SP13, after the gazing point separation, the calculating portion 1 calculates the head movement between gazing points, the eye movement, and the amplitude and head share of the movement of the line-of-sight obtained by adding the head and eye movements, and outputs the result to the output portion 4. The results are as shown in FIGS. 11 and 12. FIG. 11 shows an example of the amplitude of the line-of-sight obtained by adding the head movement and the eye movement between gazing points. FIG. 12 shows an example of head share with respect to the line-of-sight obtained by adding the head movement and the eye movement between gazing points. As is apparent from FIG. 11, there is an undershoot of 20° or more in the case of a patient of Alzheimer's disease as compared with the healthy person with respect to a target of, for example, 50°, which means that the gazing is imperfect. Accordingly, in step SP14, the calculating portion 1 discriminates a healthy person from a patient of Alzheimer's disease dependent on whether or not the gazing is imperfect. The determination of the gazing point is disclosed in, for example, Japanese Patent Laying-Open No. 2-156199 in which the velocity of the line-of-sight is used as a reference.

As is apparent from FIG. 12, the head share is decreased as the age is advanced in case of healthy persons. However, the head share of the patient of the Alzheimer's disease is further decreased and it is as small as 20% or less. Therefore in step SP15, the calculating portion 1 compares the ratio of decrease of the head share, and referring to the ratio of the head share, it determines the advance of the phenomena of aging and the advance of Alzheimer's disease.

When the processes in the steps SP1–SP15 are finished, the calculation portion 1 provides the determinations such as shown in the following table 1.

TABLE 1

DETERMINATION SHEET

| Name of Patient | (1) Number of Stepwise Eye Movement | (2) Anisotropy in velocity in left/right directions | (3) Decrease of velocity of Head Movement | (4) Imperfect Gazing | (5) Decrease of Head Share |
| --- | --- | --- | --- | --- | --- |
| ABC | o | o | o | o | o |
| DEF | o | o | x | x | o |
| XYZ | x | x | o | o | o |

By using such a sheet for determination, referring to the results of FIGS. 8–12 provided simultaneously, the doctor can discriminates the advance of the phenomena of aging from the advance of the Alzheimer's disease quickly.

The output portion 4 shown in FIG. 1 is not limited to a CRT display, and the output may be provided to a telephone circuit through a printer or a modem.

As described above, in accordance with this embodiment of the present invention, targets are presented to a subject, the eye movement of the subject at that time is detected, the spatial movement of the line-of-sight of the subject is calculated in response to the detected output and it is determined whether or not the disease is related to the brain function. Therefore, by referring to the movement of the line-of-sight, Alzheimer's disease can be immediately discriminated from the cerebrovascular disease, and this invention is promising in the field of clinical diagnosis and in the field of rehabilitation.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A medical diagnostic apparatus utilizing line-of-sight detection for diagnosing a disease related to brain function by detecting the line-of-sight of a subject, comprising:

eye movement detecting means for detecting eye movement of said subject;

target presenting means for presenting a target to said subject;

calculating means responsive to a detection output from said eye movement detecting means while said subject is gazing at a target presented by said target presenting means for calculating spatial movement of the line-of-sight of said subject to determine whether or not the disease is related to brain function; and output means for outputting the movement of the line-of-sight calculated by said calculating means and information indicating whether or not the disease is related to the brain function; and head movement detecting means for detecting head movement of said subject, wherein said calculating means include means responsive to a detection output from said head movement detecting means while said subject is gazing at the target and to the detection output from said eye movement detecting means for detecting spatial movement of the line-of-sight of said subject to output a result to said output means, and said target presenting means includes means for presenting targets from different angles with respect to said subject.

2. A medical diagnostic apparatus utilizing line-of-sight detection for diagnosing a disease related to brain function by detecting the line-of-sight of a subject, comprising:

eye movement detecting means for detecting eye movement of said subject;

target presenting means for presenting a target to said subject;

calculating means responsive to a detection output from said eye movement detecting means while said subject is gazing at a target presented by said target presenting means for calculating spatial movement of the line-of-sight of said subject to determine whether or not the disease is related to brain function;

output means for outputting the movement of the line-of-sight calculated by said calculating means and information indicating whether or not the disease is related to the brain function; and head movement detecting means for detecting head movement of said subject, wherein said target presenting means include means for presenting targets from different angles with respect to said subject, and said calculating means include means responsive to the detection output from said head movement detecting means for calculating a rotation velocity component of the head movement of said subject to output a result to said output means.

3. A medical diagnostic apparatus utilizing line-of-sight detection for diagnosing a disease related to brain function by detecting the line-of-sight of a subject, comprising:

eye movement detecting means for detecting eye movement of said subject;

target presenting means for presenting a target to said subject;

calculating means responsive to a detection output from said eye movement detecting means while said subject is gazing at a target presented by said target presenting means for calculating spatial movement of the line-of-sight of said subject to determine whether or not the disease is related to brain function;

output means for outputting the movement of the line-of-sight calculated by said calculating means and information indicating whether or not the disease is related to the brain function; and head movement detecting means for detecting head movement of said subject, wherein said target presenting means include means for presenting targets from different angles with respect to said subject, and said calculating means include means responsive to the detection output from said head movement detecting means for calculating a translational velocity component of the head movement of said subject to output a result to said output means.

4. A medical diagnostic apparatus utilizing line-of-sight detection for diagnosing a disease related to brain function by detecting the line-of-sight of a subject, comprising:

eye movement detecting means for detecting eye movement of said subject;

target presenting means for presenting a target to said subject;

calculating means responsive to a detection output from said eye movement detecting means while said subject is gazing at a target presented by said target presenting means for calculating spatial movement of the line-of-sight of said subject to determine whether or not the disease is related to brain function; and output means for outputting the movement of the line-of-sight calculated by said calculating means and information indicating whether or not the disease is related to the brain function, wherein said target presenting means include means for presenting targets from different angles with respect to said subject, said calculating means include means responsive to the detection output from said eye movement detecting means for calculating the velocity component of the eye movement of said subject to output a result to said output means, and said calculating means include means for counting the number of the stepwise eye movements for comparing an anisotropy in velocity between left/right directions to output a result to said output means.

* * * * *